United States Patent [19]

Huibers et al.

[11] 4,431,850

[45] Feb. 14, 1984

[54] LOW TEMPERATURE HYDRODEALKYLATION OF ALKYLATED PHENOLS

[75] Inventors: Derk T. A. Huibers, Pennington; Cheng-Yih Jenq, Princeton, both of N.J.

[73] Assignee: HRI, Inc., Gibbsboro, N.J.

[21] Appl. No.: 319,771

[22] Filed: Nov. 9, 1981

[51] Int. Cl.³ .............................................. C07C 37/50
[52] U.S. Cl. ...................................... 568/805; 568/799
[58] Field of Search ................................. 568/799, 805

[56] References Cited

U.S. PATENT DOCUMENTS

| | | | |
|---|---|---|---|
| 3,284,513 | 11/1966 | Dedinas et al. | 568/805 |
| 3,284,514 | 11/1966 | Dedinas et al. | 568/805 |
| 4,230,895 | 10/1980 | Daly | 568/805 |

FOREIGN PATENT DOCUMENTS

| | | | |
|---|---|---|---|
| 786389 | 5/1968 | Canada | 568/805 |
| 786390 | 5/1968 | Canada | 568/805 |
| 787970 | 6/1968 | Canada | 568/805 |

*Primary Examiner*—Werren B. Lone
*Attorney, Agent, or Firm*—Vincent A. Mallare; Fred A. Wilson

[57] ABSTRACT

A process for thermal dealkylation of alkylated phenols feedstocks, which comprises reacting a feed mixture containing mono and poly-alkylated phenols and gaseous hydrogen at temperature ranging from about 900° to about 1100° F. at hydrogen partial pressure of 300 to 1600 psig, and space velocity of 0.2 to 3.0 volume feed/hr/volume of reactor to produce a phenol-containing product at increased selectivity and yield of phenol. For feedstream mixtures containing more than about 10 W % phenols, a prior distillation step is preferably used to remove the excessive phenol as product and thus avoid undesired dehydroxylation reactions in the hydrodealkylation step to which the feed phenol concentration is usually about 2–8 W %.

11 Claims, 2 Drawing Figures

DEALKYLATION SELECTIVITY RATIO k₁/k₂ vs. REACTION TEMPERATURE $k_1$ = FIRST ORDER DEALKYLATION CONSTANT
$k_2$ = FIRST ORDER DEHYDROXYLATION CONSTANT

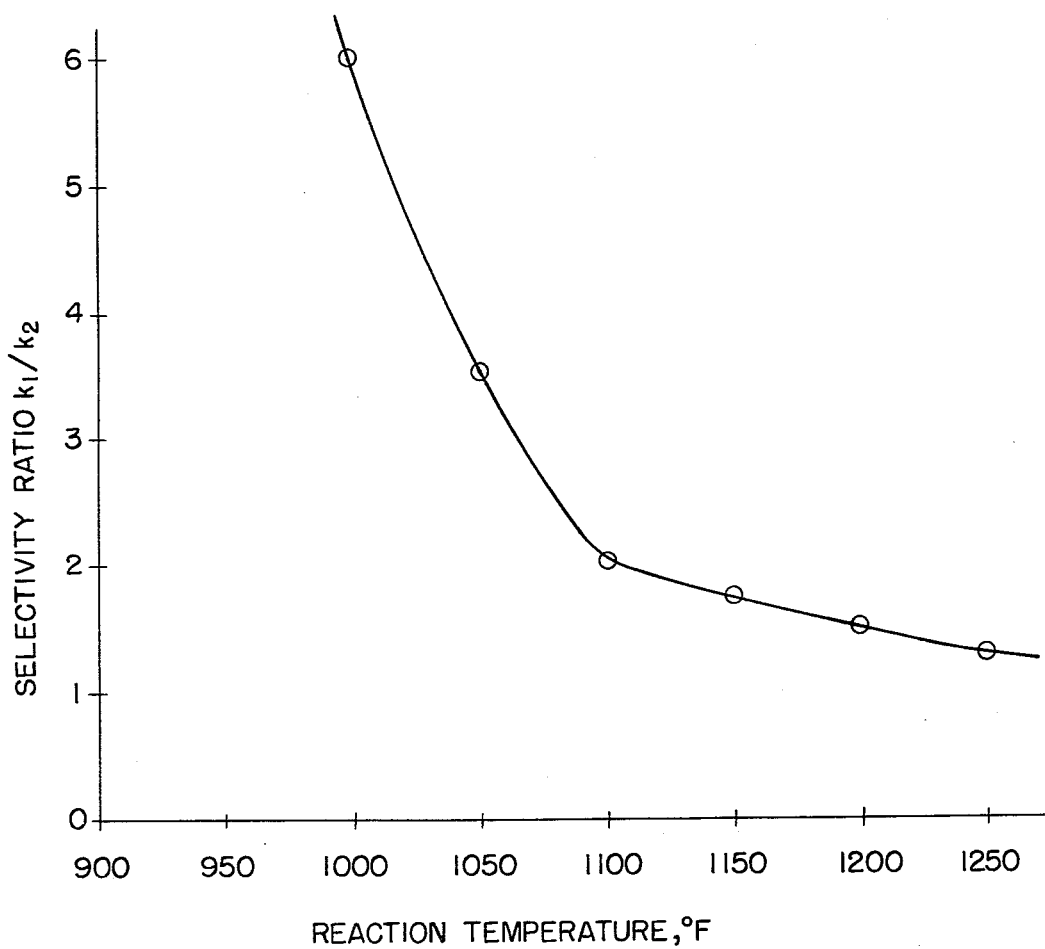

LOW TEMPERATURE HYDRODEALKYLATION OF ALKYLATED PHENOLS

BACKGROUND OF INVENTION

This invention pertains to a process for thermal hydrodealkylation of alkylated phenols to produce increased yields of phenol product. It pertains particularly to such thermal hydrodealkylation process utilizing reaction temperatures below about 1100° F. (593° C.).

When a mixture of mono- and poly-alkylated phenols is subjected to hydrodealkylation reaction at elevated temperature and pressure conditions in the presence of hydrogen, but in the absence of a catalyst, to effect thermal hydrodealkylation reactions, not only are alkyl substituents removed but there is also a tendency for the hydroxyl group to be cleaved from the aromatic ring. Because phenol is usually the more desired product rather than benzene and alkylated benzenes, it is desirable to increase the selectivity of the thermal hydrodealkylation reaction to produce increased yields of phenol.

In the prior art, U.S. Pat. Nos. 3,284,513 and 3,284,514 to Dedinas et al., disclosed that selectivity to the alkyl substituents removal can be maximized and cleavage of hydroxyl group reduced by converting the mono- and poly-alkylated phenols to an extent of not more than about 88 to 92 V % conversion, when subjecting them to preferred reaction conditions of a temperature of about 900° to 1600° F. and a space velocity of about 0.2 to 3.5 volume feed/hour/volume reactor. The reaction temperature used in the examples was limited to the narrower range of 1106°-1355° F. No effect of temperature on the selectivity of dealkylation versus dehydroxylation was discovered. Also, U.S. Pat. No. 4,230,895 to Daly discloses a process for thermal dealkylation of alkylphenols at temperature of 1000°-1500° F. and total pressure of 400-800 psig in the presence of added water vapor. Although Daly discloses a reaction temperature range of 1000°-1500° F., his experiments were confined to 1150° and 1200° F. with added water vapor; therefore, he did not recognize any yield advantage of using reaction temperatures below about 1100° F. without added water. Thus, a need remains for further process improvements for selectively producing phenol from alkylated phenols, whereby the alkyl substituent in the alkylated phenol may be removed without simultaneously removing the hydroxyl group.

SUMMARY OF INVENTION

The present invention provides a process for thermal hydrodealkylation of alkylated phenols to produce increased yields of phenol product using a reaction temperature below about 1100° F. The process improves upon prior art processes in that lower reaction temperatures are used, as it was unexpectedly found that selectivity for phenol is related to the temperature at which the thermal hydrodealkylation reaction is effected. Specifically, it was found that a mixture of mono- and poly-alkylated phenols, such as cresols, methyl-ethyl phenols and xylenols, can be hydrodealkylated and the selectivity for phenols can be improved by subjecting the mixture to a reaction temperature as low as the reaction rate permits, such as at a temperature below about 1100° F. (593° C.) and preferably at about 900°-1050° F. (482°-566° C.). At such lower temperature, retention of the hydroxyl group on the aromatic ring is increased as compared to reactions occurring at higher temperatures while alkyl groups are effectively removed. The hydrogen to phenol molar ratio in the feed mixture should be at least about 1.0, and usually need not exceed about 6. Feedstream space velocity should be within the range of 0.2-3.0 $V_f/hr/V_r$ (volume of feed per hour per volume of reactor).

Based on our results, the preferred embodiment of this invention comprises reacting a mixture of mono- and poly-alkylated phenols which usually contain not more than about 10 W % phenol, with about 2 to 5 moles of hydrogen per mole phenols mixture, at temperature of about 900° to 1050° F. hydrogen partial pressure of about 300 to 1500 psi and space velocity of about 0.5 to 2.5 $V_f/hr/V_r$, and thereafter recovering phenol product from the reactor effluent. The phenol concentration in the feedstream should usually not exceed about 10 W % to avoid undesired losses due to dehydroxylation reactions and preferably should contain about 2–8 W % phenol. Accordingly, feedstreams containing phenol concentrations exceeding about 10 W % are preferably subjected to a prior distillation step to remove the excess phenol as product then the remaining stream is thermally hydrodealkylated at temperature below about 1100° F. (593° C.).

DESCRIPTION OF DRAWINGS

FIG. 2 is a graph showing the improved results of thermal hydrodealkylation reactions at temperatures between 950° and 1250° F.

DESCRIPTION OF PREFERRED EMBODIMENT

Figure 1:
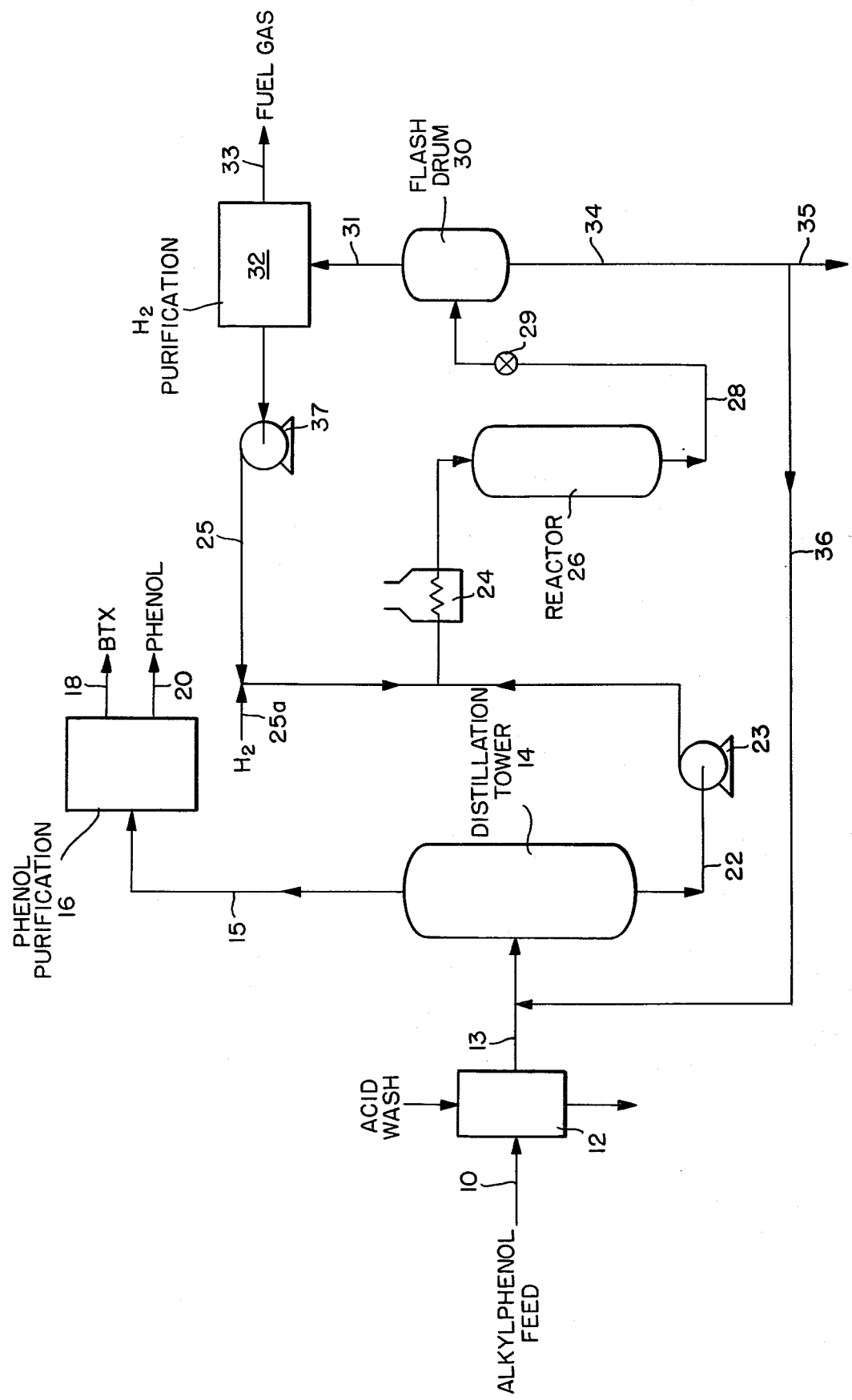
FIG. 1 is a process flow diagram showing the essential thermal hydrodealkylation steps of the invention.

As shown in FIG. 1, an alkylphenol feedstream at 10, containing at least about 10 W % phenol and usually 20–50 W % phenol with the balance being cresols and ethylphenols, is usually acid washed at 12 to remove nitrogen-containing compounds and tars. The washed alkylphenols material is then passed to phenol distillation tower 14 for removal of any phenol exceeding about 10 W % concentration. Distillation conditions used are usually within the range of 320°–370° F. temperature and 14–16 psia pressure. The resulting overhead stream 15 is passed to phenol purification unit 16 for conversion into a product stream 18 containing a benzene-toluene-xylene mixture and a phenol product stream 20 containing 80–99.5 W % phenol.

From phenol distillation tower 14, the bottoms liquid stream 22 usually containing 2–8 W % phenols with the balance alkyl-phenols, is pressurized at 23 preheated at 24 and passed to phenol hydrodealkylation reactor 26 for the hydrodealkylation reaction at conditions selected to increase the phenol product yield relative to other materials such as benzene, toluene and xylene. The hydrogen required is added at 25. Broad reaction conditions used in reactor 26 are within the ranges of 900°–1100° F. temperature and 300–1600 psig hydrogen partial pressure the feed rate or space velocity is usually between 0.2–3.0 $V_f/hr/V_r$ reactor. Preferred reaction conditions are 950°–1050° F. temperature, 300–1500 psig hydrogen partial pressure, and space velocity of 0.5–2.5 $V_f/hr/V_r$. Although reactor 26 is shown arranged for downflow of the feedstream which is usually preferred, an upflow reactor arrangement could be used.

Reactor effluent stream 28 containing increased phenol is pressure-reduced at 29 and passed to flash drum 30. The resulting vapor portion 13 containing appreciable hydrogen is passed to hydrogen purification step 32. Recovered hydrogen at 25 is recycled to reactor 26, and fresh makeup hydrogen is added at 25a as needed. A fuel gas product stream is withdrawn at 33. From flash drum 30 the liquid portion at 34 contains increased phenols and some unconverted cresols, ethyl phenols and xylenol materials, and is recycled to phenol distillation tower 14 for further processing to concentrate the phenol product. A purge stream is usually withdrawn at 35 to remove undesired materials.

The invention will be illustrated by reference to the following example, which should not be construed as limiting the scope of the invention.

EXAMPLE 1

Thermal hydrodealkylation experiments were performed on an alkylphenol feed material at reaction temperatures of 1000° to 1250° F., at hydrogen partial pressures of 450 and 1200 psig, at hydrogen rates of 3–4 moles $H_2$ per mole feed, and at liquid space velocities of about 0.5 to 2.0 $V_f/hr/V_r$. The liquid feed contained a mixture of cresols, xylenols and other poly-alkylated phenols of various compositions, as shown in Table 1. The results of the runs were analyzed and the reaction rates for removal of alkyl groups (dealkylation) and removal of hydroxyl groups (dehydroxylation) were measured.

The first order rate constants of dealkylation, denoted as $k_1$ and the first order rate constants of dehydroxylation, denoted as $k_2$, were found by regression analysis procedures to be constants dependent only on temperature and hydrogen partial pressure. The ratio of these constants expressed as $k_1/k_2$, which measures the relative selectivity to dealkylation, unexpectedly showed a trend of increasing with respect to decreases in reaction temperature. The relationship between the selectivity, expressed as the ratio of $k_1/k_2$, and the reaction temperature is shown in FIG. 2, which shows a large increase in selectivity to hydrodealkylation when reaction temperature is below about 1100° F.

TABLE 1

THERMAL HYDRODEALKYLATION OF A MIXED PHENOLS FEED

| Run. No. | 1 | 2 | 3 |
|---|---|---|---|
| Feed Composition, W % | | | |
| Phenol | 6.10 | 6.10 | 6.10 |
| Cresols | 57.82 | 57.82 | 57.82 |
| Ethyl phenols | 7.50 | 7.50 | 7.50 |
| Xylenols | 21.48 | 21.48 | 21.48 |
| Toluene | 0.22 | 0.22 | 0.22 |
| Xylenes | 0.23 | 0.23 | 0.23 |
| Unknown | 5.92 | 5.92 | 5.92 |
| Reaction Conditions | | | |
| Temperature, °F. | 1000 | 1000 | 1100 |
| $H_2$ Pressure, psig | 1200 | 1150 | 1200 |
| $H_2$ mole/feed mole | 3.62 | 3.74 | 3.56 |
| Space velocity, $Hr^{-1}$ | 1.00 | 1.22 | 1.04 |
| Contact Time, sec | 107 | 82 | 98 |
| Product Composition, W % of Feed | | | |
| Phenol | 16.29 | 10.95 | 17.50 |
| Cresols | 43.99 | 51.80 | 33.08 |
| Ethyl phenols | 7.03 | 7.57 | 7.30 |
| Xylenols | 13.24 | 17.18 | 11.96 |
| Benzene | 1.47 | 0.25 | 3.09 |
| Toluene | 0.71 | 0.90 | 8.03 |
| Ethyl benzene | 0.18 | 0.19 | 0.75 |
| Xylenes | 0.26 | 0.22 | 1.29 |
| Unknown | 6.84 | 6.60 | 4.65 |
| Selectivity, Weight Ratio | | | |
| Phenol/Benzene | 11.08 | 43.8 | 5.66 |
| Phenol Selectivity Index | 4.69 | 4.37 | 0.90 |

Table 1 shows specific results of thermal hydrodealkylation experiments performed on a typical mixed phenols feed, and illustrates that phenol/benzene yield weight ratio increased appreciably as the reaction temperature was reduced from 1100° to 1000° F. Also, from the above results, it is apparent that the present invention provides an improved hydrodealkylation process whereby the phenol selectivity is substantially improved. The net phenol selectivity index provides a better comparison of the hydrodealkylation results, and is the ratio of net phenol in the product stream to the net amounts of aromatic products such as benzene, ethylbenzene, toluene and zylene in the product stream.

Although we have disclosed certain preferred embodiments of our invention, it is recognized that various modifications can be made thereto, all within the spirit and scope of the invention, which is defined by the following claims.

We claim:

1. A process for thermal hydrodealkylation of alkylated phenols feedstock to produce phenol, comprising admixing the feed solution comprising a mixture of alkylated phenols selected from the group consisting of cresols, methyl-ethyl phenols and xylenols with hydrogen to provide a hydrogen to phenol molar ratio of at least about 1.0 and reacting said mixture at temperature ranging from about 900° to about 1050° F., to produce increased yield of phenol product.

2. The process of claim 1, wherein hydrogen to phenol molar ratio is from about 2 to 6.

3. The process of claim 1, wherein the dealkylation reaction occurs at a hydrogen partial pressure of about 300 to 1600 psig.

4. The process of claim 1, wherein the reaction is carried out at a volume hourly space velocity from about 0.2 to 3.0 volume alkyl phenol/hour/volume reactor.

5. The process of claim 1, wherein the hydrogen to feed molar ratio is from about 2.5 to 5.0, the reaction temperature is from about 900° to 1050° F., the hydrogen partial pressure is from about 350 to 1500 psig, the volume hourly space velocity is from about 0.5 to 2.5 volume alkyl phenol/hour/volume reactor.

6. The process of claim 1, wherein the hydrogen to feed molar ratio is from about 3.0 to 4.0, the reaction temperature is from about 950° to 1050° F., the hydrogen partial pressure is from about 700 to 1200 psig, the volume hourly space velocity is from about 0.8 to 1.6 volume alkyl phenol/hour/volume reactor volume.

7. The process of claim 1, wherein the alkylated phenols feedstock contains not more than about 10 W % phenol.

8. The process of claim 7, wherein the alkylated phenols feedstream is provided from an distillation step upstream of the thermal hydrodealkylation step.

9. A process for thermal hydrodealkylation of alkylated phenols feedstocks to produce phenol, comprising:
 (a) admixing a feed comprising at least one of an alkylated phenol selected from the group consisting of cresols, methyl-ethyl phenols and xylenols with hydrogen, to provide hydrogen to feed molar ratio from about 2.0 to about 6.0; and (b) reacting said solution at a temperature from about 950° to about 1050° F. at hydrogen partial pressure from about 300 to about 1600 psig, and volume hourly space velocity from about 0.5 to about 3.0 volume alkyl phenol/hour volume reactor, to produce increased yield of phenol product.

10. The process of claim 9, wherein the alkylated phenols feedstock contains about 2–8 W % phenol.

11. A process for thermal hydrodealkylation of phenols to form a phenol-containing product, comprising reacting a feed solution comprising a mixture of alkylated phenols selected from the group consisting of cresols, methyl-ethyl phenols and xylenols with hydrogen at hydrogen partial pressure from about 300 to 1500 psig, and space velocity of 0.2–3.5 volume feed/hour/volume reactor, wherein the improvement comprises maintaining a reaction temperature between about 900° and 1050° F. and a hydrogen to phenol molar ratio between about 1.0 and 6 to produce increased yield of phenol product.

* * * * *